US005756841A

United States Patent [19]

Desmarteau et al.

[11] Patent Number: 5,756,841
[45] Date of Patent: May 26, 1998

[54] PROCESS FOR PREPARING FLUOROXY-OR CHLOROXY-PERFLUOROACYLEFLUORIDES

[75] Inventors: Derryl D. Desmarteau, Clemson, S.C.; John David O. Anderson, Augusta, Ga.; Walter Navarrini, Boffalora Ticino, Italy

[73] Assignee: Ausimont S.p.A., Italy

[21] Appl. No.: 683,461

[22] Filed: Jul. 18, 1996

[30] Foreign Application Priority Data

Jul. 19, 1995 [IT] Italy ............... MI95A01556

[51] Int. Cl.$^6$ .................................................. C07C 53/38
[52] U.S. Cl. ........................................................ 562/849
[58] Field of Search ............................................. 562/849

[56] References Cited

U.S. PATENT DOCUMENTS

| | | |
|---|---|---|
| 3,442,927 | 5/1969 | Thompson ............... 562/849 |
| 3,715,378 | 2/1973 | Sianesi et al. . |
| 3,770,792 | 11/1973 | Sianesi et al. . |
| 3,810,874 | 5/1974 | Mitsch et al. . |
| 4,647,413 | 3/1987 | Savu . |
| 4,827,024 | 5/1989 | Guglielmo et al. . |
| 4,900,872 | 2/1990 | Guglielmo et al. . |
| 5,013,472 | 5/1991 | Marraccini et al. . |
| 5,149,842 | 9/1992 | Sianesi et al. . |
| 5,258,110 | 11/1993 | Sianesi et al. . |

FOREIGN PATENT DOCUMENTS

| | | |
|---|---|---|
| 0 027 009 | 4/1981 | European Pat. Off. . |
| 0 148 482 | 7/1985 | European Pat. Off. . |
| 0 239 123 | 9/1987 | European Pat. Off. . |
| 0 259 817 A2 | 3/1988 | European Pat. Off. . |
| 0 267 627 | 5/1988 | European Pat. Off. . |
| 0 404 076 | 3/1995 | European Pat. Off. . |
| 1104482 | 2/1968 | United Kingdom . |

OTHER PUBLICATIONS

Kennedy et al., "Reaction of Carbonyl Fluoride with Fluorine in the Presence of Various Fluorides as Catalysts", J. of Fluorine Chem., 1973/1974, pp. 41–54.

Ruff et al., "A Simple Synthesis of Fluoroxyperfluoroalkyl Compounds", letter to J. Am. Chem. Soc., 88: (19).: pp. 4531–4532 (Oct. 5, 1966).

Primary Examiner—Paul J. Killos
Attorney, Agent, or Firm—Finnegan, Henderson, Farabow, Garret & Dunner, L.L.P.

[57] ABSTRACT

Process for preparing fluoroxy- or chloroxy-perfluoroacylfluorides $FC(O)-R_F-CF_2OX$, wherein $R_F$ is a perfluoroalkylenic or perfluoropolyoxyalkylenic chain, X is —F or —Cl, by fluorination or chlorofluorination of the corresponding perfluorodiacylfluoride $FC(O)-R_F-C(O)F$ with X—F in the presence of an hydrogenfluoride corresponding to the formula $MeF_y \cdot zHF$, wherein: Me is an alkaline or alkaline-earth metal, y is 1 when Me is an alkaline metal, or y is 2 when Me is an alkaline-earth metal; z is comprised between 0.5 and 4.

9 Claims, No Drawings

PROCESS FOR PREPARING FLUOROXY-OR CHLOROXY-PERFLUOROACYLEFLUORIDES

The present invention relates to a process or the preparation of fluoroxy- or chloroxy-perfluoroacylfluorides by catalytic fluorination or chlorofluorination of the corresponding diacylfluorides.

It is known that perfluoroacylfluorides $R_F$—C(O)F, wherein $R_F$ is a perfluoroalkylic chain, can be used as a substrate for preparing the corresponding fluoroxy- or chloroxy-compounds $R_F$—$CF_2OX$ (X=—F, —Cl), by fluorination or chlorofluorination with F—X (X=—F, —Cl) in the presence of a fluoride of an alkaline or alkaline-earth metal as catalyst (see for instance Ruff J. K. et al in J. Am. Chem. Soc. 88:19, 1966, or also U.S. Pat. No. 4,827,024).

According to the experimentation carried out by the Applicant, the application of such process to perfluorodiacylfluorides FC(O)—$R_F$—C(O)F exclusively leads to the obtainment of the corresponding difluoroxy- or dichloroxy-compounds $XOCF_2$—$R_F$—$CF_2OX$. In other words it is not possible to obtain a selective (chloro)fluorination of only one of the acylfluoride groups also when one operates with a molar ratio between diacylfluoride and X—F around 1:1. Such process results therefore not suitable to the preparation of fluoroxy- or chloroxy-perfluoroacylfluorides FC (O)—$R_F$—$CF_2OX$.

The Applicant has now surprisingly found that it is possible to carry out a selective fluorination or chlorofluorination of perfluorodiacylfluorides FC(O)—$R_F$C(O)F obtaining the corresponding fluoroxy- or chloroxy-perfluoroacylfluorides FC(O)—$R_F$—$CF_2OX$ by reaction with X—F in the presence of an hydrogenfluoride corresponding to the formula $MeF_y \cdot zHF$ as defined hereinunder.

Object of the present invention is therefore a process for preparing fluoroxy- or chloroxy-perfluoroacylfluorides FC(O)—$R_F$—$CF_2OX$, wherein $R_F$ is a perfluoroalkylenic or perfluoropolyoxyalkylenic chain, X is —F or —Cl, which comprises reacting the corresponding perfluorodiacylfluoride FC(O)—$R_F$—C(O)F with X—F in the presence of an hydrogenfluoride corresponding to the formula $MeF_y \cdot zHF$, wherein: Me is an alkaline or alkaline-earth metal, y is 1 when Me is an alkaline metal, or y is 2 when Me is an alkaline earth metal; z is comprised between 0.5 and 4, preferably between 0.5 and 2. Preferably X is —F.

By the prefix "perfluoro" are meant per(halo)fluorinated organic radicals, wherein the carbon atoms are completely saturated by fluorine atoms, and optionally also by chlorine atoms.

A further object of the present invention are fluoroxy- or chloroxy-perfluoroacylfluorides FC(O)—$R_F$—$CF_2OX$ as defined above. Such products result new and, analogously to the known RF—$CF_2OX$ compounds, can be used as intermediates for preparing other fluorinated products, exploiting the reactivity of the fluoroxy or chloroxy terminal group towards the compounds having ethylenic unsaturation. They can for instance be used for the synthesis of perfluorohaloethers by reaction with halogenated olefins, as described for instance in U.S. Pat. Nos. 4,900,872, 5,013,472, EP-404, 076, or with fluorovinylethers, as described in EP patent 267,627. Unlike the known fluoroxy- or chloroxy compounds, which are end-capped with a perfluoroalkylic group, the ones object of the present invention are functionalized with an acylfluoride group. This is an evident advantage, since the acylfluoride group can be in its turn transformed into other functional groups, such as carboxyl, amide, ester groups, etc., to prepare, for instance, functionalized fluorinated monomers similar to those described in EP-27,009.

The perfluorodiacylfluorides FC(O)—$R_F$—C(O)F are known products. As indicated above, $R_F$ can be a perfluoroalkylenic chain, optionally containing chlorine and/or one or more atoms of ether oxygen, generally having from 1 to 12, preferably from 2 to 8, carbon atoms.

Alternatively, $R_F$ can be a perfluoropolyoxyalkylenic group, that is a group consisting of one or more perfluorinated oxyalkylenic repeating units, optionally containing chlorine, statistically distributed along the chain. Such repeating units can be selected for instance from: —(CF($CF_3$)$CF_2$O)—; —($CF_2CF(CF_3)O$)—; —($CF_2CF_2O$)—; —($CFW_1O$)— wherein $W_1$ is —F or —$CF_3$; —($CW_2W_3$—$CF_2CF_2O$)— wherein $W_2$ and $W_3$, equal to or different from each other, are F or Cl. The number of repeating units is such that the number average molecular weight $M_n$ of $R_F$ is comprised between 300 and 2,000, preferably between 400 and 1,000.

In particulr, $R_F$ can be selected from the following classes:

(a)

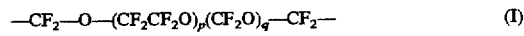

wherein:
p and q are numbers such that the q/p ratio is comprised between 0.5 and 2 and the molecular weight is comprised in the range indicated above;

(b)

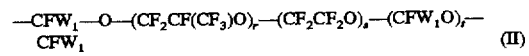

wherein:
$W_1$ is —F or —$CF_3$; r, s and t are numbers such that the r+s is comprised between 1 and 50, the t/(r+s) ratio is comprised between 0.01 and 0.05 and the molecular weight is comprised in the range indicated above;

(c)

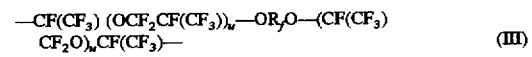

wherein:
$R_f$ is a $C_1$–$C_8$ perfluoroalkylene; u is a number such that the molecular weight is comprised in the range indicated above.

(d)

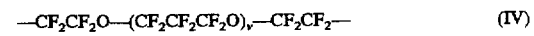

wherein:
v is a number such that the molecular weight is comprised in the range indicated above;

(e)

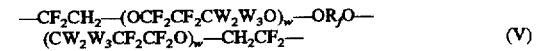

wherein:
$R_f$ is a $C_1$–$C_8$ perfluoroalkylene; $W_2$ and $W_3$, equal to or different from each other, are F or Cl; w is a number such that the molecular weight is comprised in the range indicated above;

(f)

—CF$_2$—O—(CF$_2$CF$_2$O)$_x$—CF$_2$— (VI)

wherein:

x is a number such that the molecular weight is comprised in the range indicated above.

The above mentioned difunctional perfluoropolyoxyalkylenes having —C(O)F terminals can be prepared according to what described, for instance, in patents GB 1,104,482, U.S. Pat. Nos. 3,715,378, 3,770,792, 4,647,413, EP 148,482, U.S. Pat. No. 3,810,874, EP 239,123, U.S. Pat. Nos. 5,149,842, 5,258,110.

The catalyst having the formula MeF$_y$.zHF as defined above can be prepared by treating the corresponding solid MeF$_y$ fluoride with gaseous HF or with a HF aqueous solution (see for instance R. C. Kennedy and G. H. Cady, J. Fluorine Chem., 3 (1973/74), p. 42–54). Preferably Me is an alkaline metal, and still more preferably is selected between Cs and K.

The reaction can be carried out by reacting the perfluorodiacylfluoride, pure or dissolved in a suitable solvent, with gaseous X—F in the presence of the catalyst in the solid state. In order to favour the heat exchange, the catalyst can be supported or mixed with an inert material towards the fluorine, for instance cupper or its alloys. The solvent can be selected for instance from chlorofluorocarbons and hydrogenfluorocarbons optionally containing chlorine. The reaction temperature is generally comprised between −40° C. and +40° C., preferably between −20° and +10° C. The reaction pressure is not critical; for operating easiness, it is generally kept at a value around the atmospheric pressure. The molar ratio beetween X—F and diacylfluoride substrate is generally around 1, for instance between 0.8 and 1.2, preferably between 0.9 and 1.1. The amount of hydrogenfluoride catalyst to be used can range within wide limits; generally the added amount is such as to have a molar ratio between catalyst and diacylfluoride substratum comprised between 20:1 and 1:20.

Some working examples of the present invention are reported hereinafter, whose purpose is only illustrative but not limitative of the scope of the invention itself.

EXAMPLE 1

Preparation of the CsF—HF catalyst 13.68 g (90.05 mmoles) of CsF were placed in a stainless steel AISI 316 cylinder, having 120 mm×50 mm sizes. . The cylinder was sealed, connected to a vacuum line and evacuated. By means of the vacuum line 4.51 g (225.50 mmoles) of HF were condensed therein. The mixture was heated to 110° C. for 12 hours. The cylinder was then cooled at 25° C., let stay for 12 hours and then heated again to 135° C. for 2 hours, removing the HF excess through the vacuum line. The cylinder was then open in a dry box, and 14.91 g of CsF.HF were discharged therefrom (yield: 96.3%).

Reaction between FC(O)—CF$_2$CF$_2$—C(O)F and F$_2$ in the presence of CsF.HF

A 150 ml passivated stainless steel AISI 316 cylinder, containing 2.54 g (14.8 mmoles) of CsF.HF prepared as above was connected to a vacuum line, cooled at −196° C. and evacuated. By means of the vacuum line 1.50 mmoles of perfluorosuccinylfluoride and 1.51 mmoles of F$_2$ were condensed therein. The mixture was let stay at −10° C. for 8 hours. The cylinder was cooled at −196° C., and every trace of residual F$_2$ was removed by means of the vacuum line. The cylinder was heated up to 25° C., while the volatile products were sucked and gathered in a trap at −196° C. 1.66 mmoles of a mixture of products were obtained, which, by $^{19}$F-NMR analysis at −20° C., showed the following composition: FC(O)—CF$_2$CF$_2$CF$_2$—OF (80.6%), CF$_3$CF$_2$C(O)F (11.9%), and C(O)F$_2$ (7.4%). The yield in fluoroxy-perfluoroacylfluoride was equal to 89%.

Main bands of the IR spectrum of the product FC(O)—CF$_2$CF$_2$CF$_2$—OF (cm$^{-1}$, gas phase): 1888 (vs), 1325 (w), 1287 (m), 1225 (vs), 1133 (s), 1062 (m), 1003 (w), 959 (m), 922 (w), 888 (m), 809 (m), 780 (vw), 763 (w), 708 (w), 687 (w).

Main $^{19}$F—NMR bands of the product F$^A$O—CF$^B$$_2$CF$^C$$_2$CF$^D$$_2$—C(O)F$^E$ (ppm, CDCl$_3$, 248K): A+147.4 (s, 1F), B−91.7 (m, 2F), C−123.0 (s, 2F), D−119.1 (m, 2F), E+26.9 (m, 1F) (vs=very strong, s=strong, m=medium, W=weak, vw=very weak).

EXAMPLE 2 (comparative)

Reaction between FC(O)—CF$_2$CF$_2$—C(O)F and F$_2$ in the presence of CsF

Example 1 was repeated by using as catalyst, instead of CsF—HF, 2.54 g (16.7 mmoles) of CsF. At the end of the reaction, 1.6 mmoles of a mixture of products were obtained, which by $^{19}$F—NMR analysis at −20° C., showed the following composition: FC(O)—CF$_2$CF$_2$—C(O)F (46%), FO—(CF$_2$)$_4$—OF (54%). No trace of FC(O)—CF$_2$CF$_2$CF$_2$—OF was noticed.

EXAMPLE 3

Reaction between FC(O)—CF$_2$CF$_2$—C(O)F and F$_2$ in the Presence of KF·HF

The cylinder of example 1, containing 2.53 g (32.4 mmoles) of KF·HF (commercial product by Aldrich Chemical Co. in powder form) was connected to a vacuum line, cooled at −196° C. and evacuated. By means of the vacuum line 1.50 mmoles of perfluorosuccinylfluoride and 3.33 mmoles of F$_2$ were condensed therein. The mixture was let stay at −10° C. for 8 hours. The cylinder was cooled at −196° C., and all traces of residual F$_2$ was removed by means of the vacuum line. The cylinder was heated up to 25° C., while the volatile products were sucked and gathered in a trap at −196° C. 1.57 mmoles of a mixture of products were obtained, which, by $^{19}$F—NMR analysis at −20° C., showed the following composition: FC(O)—CF$_2$CF$_2$CF$_2$—OF (79%), FO—(CF$_2$)$_4$—OF (19%), and C(O)F$_2$ (2%). The yield in fluoroxy-perfluoroacylfluoride was equal to 82%.

EXAMPLE 4 (comparative)

Reaction between FC(O)—CF$_2$CF$_2$—C(O)F and F$_2$ in the presence of KF

Example 1 was repeated by using as catalyst, instead of KF·HF, 2.54 g (43.7 mmoles) of KF. At the end of the reaction, 1.6 mmoles of a mixture of products were obtained, which by $^{19}$F—NMR analysis at −20° C., showed the following composition: FC(O)—CF$_2$CF$_2$—C(O)F (51%), FO—(CF$_2$)$_4$—OF (49%). No trace of FC(O)—CF$_2$CF$_2$CF$_2$—OF was noticed.

We claim:

1. Process for preparing fluoroxy- or chloroxy-perfluoroacylfluorides FC(O)—R$_F$—CF$_2$OX, wherein R$_F$ is a perfluoroalkylenic or perfluoropolyoxyalkylenic chain, X is —F or —Cl; which comprises selectively reacting the corresponding perfluorodiacylfluoride FC(O)—$R_F$—C(O)F with X—F in the presence of an hydrogenfluoride corresponding to the formula $MeF_y \cdot zHF$, wherein: Me is an alkaline or alkaline-earth metal, y is 1 when Me is an alkaline metal, or y is 2 when Me is an alkaline-earth metal; z is comprised between 0.5 and 4.

2. Process according to claim 1, wherein $R_F$ is a perfluoroalkylenic chain, optionally containing chlorine and/or one or more atoms of ethereal oxygen, having from 1 to 12 carbon atoms.

3. Process according to claim 1, wherein $R_F$ is a perfluoropolyoxyalkylenic chain consisting of one or more perfluorinated oxyalkylenic repeating units, optionally containing chlorine, statistically distributed along the chain.

4. Process according to claim 3, wherein the oxyalkylenic repeating units are selected from:

—(CF(CF$_3$)CF$_2$O)—;  —(CF$_2$CF(CF$_3$)O)—; —(CF$_2$CF$_2$O)—; —(CFW$_1$O)— wherein W$_1$ is —F or —CF$_3$;  —(CW$_2$W$_3$—CF$_2$CF$_2$O)— wherein W$_2$ and W$_3$, equal to or different from each other, are F or Cl, the number of repeating units being such that the number average molecular weight $M_n$ of $R_F$ is comprised between 300 and 2,000.

5. Process according to any one of claims 1–4, wherein in the formula $MeF_y \cdot zHF$, z is between 0.5 and 2.

6. Process according to any one of claims 1–4, wherein in the formula $MeF_y \cdot zHF$, Me is Cs or K.

7. Process according to any one of claims 1–4, wherein the reaction is carried out at a temperature between –40° and +40° C.

8. Process according to any one of claims 1–4, wherein the molar ratio between X—F and diacylfluoride substrate is between 0.8 and 1.2.

9. Process according to any one of claims 1–4, wherein the hydrogen fluoride catalyst is present in such amount as to have a molar ratio of between 20:1 and 1:20 catalyst to diacyl-fluoride substrate.

* * * * *

UNITED STATES PATENT AND TRADEMARK OFFICE
CERTIFICATE OF CORRECTION

PATENT NO. : 5,756,841
DATED : May 26, 1998
INVENTOR(S) : Darryl D. DESMARTEAU et al.

It is certified that error appears in the above-identified patent and that said Letters Patent is hereby corrected as shown below:

Title page, column 1, item [54], line 3 of title, and col.1, line 3 "PERFLUOROACYLEFLUORIDES" should read --PERFLUOROACYLFLUORIDES--

Title page, column 1, item [75], line 1 of inventors, "Derryl" should read --Darryl--.

Signed and Sealed this

Twenty-eighth Day of July, 1998

Attest:

BRUCE LEHMAN

*Attesting Officer*　　　*Commissioner of Patents and Trademarks*